United States Patent [19]
Tsuroka et al.

[11] Patent Number: 4,954,510
[45] Date of Patent: Sep. 4, 1990

[54] ANTIVIRAL AGENT CONTAINING LACTAM COMPOUND

[75] Inventors: Takashi Tsuroka; Satoru Nakabayashi; Yuji Matsuhashi; Haruo Yamamoto; Shigeharu Inouye; Shinichi Kondo, all of Kanagawa, Japan

[73] Assignee: Meiji Seika Kaisha, Ltd., Tokyo, Japan

[21] Appl. No.: 289,152

[22] Filed: Dec. 23, 1988

[30] Foreign Application Priority Data

Dec. 25, 1987 [JP] Japan ................................. 326747
Dec. 26, 1987 [JP] Japan ................................. 328387

[51] Int. Cl.$^5$ ......................................... A61K 31/445
[52] U.S. Cl. ................................. 514/315; 514/328
[58] Field of Search ........................... 514/31 T, 328

[56] References Cited
PUBLICATIONS

Chemical Abstracts 77:122650x (1972).
Chemical Abstracts 81:91892d (1974).
Chemical Abstracts 83:79547d (1975).
Chemical Abstracts 88:99316j (1978).

Primary Examiner—Jerome D. Goldberg
Attorney, Agent, or Firm—Sughrue, Mion, Zinn, Macpeak & Seas

[57] ABSTRACT

A therapeutic and/or prophylactic agent for viral infection, particularly human immunodeficiency virus (HIV) infection, which comprises as an active ingredient a lactam compound represented by formula (I)

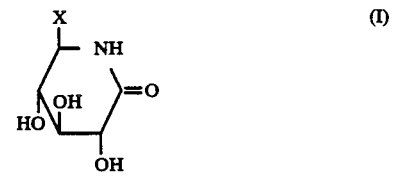

wherein X represents —COOR, wherein R represents a hydrogen atom or a straight-chain or branched-chain alkyl group having from 1 to 8 carbon atoms, or

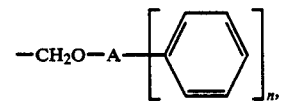

wherein n represents an integer of 2 or 3 and A represents methine when n is 2 or a quarternary carbon atom when n is 3, or a pharmaceutically acceptable salt or ester derivative thereof.

6 Claims, No Drawings

ANTIVIRAL AGENT CONTAINING LACTAM COMPOUND

FIELD OF THE INVENTION

The present invention relates to an antiviral agent comprising a lactam compound, more particularly, to a prophylactic and therapeutic agent for infections with retroviruses, particularly human immuno-deficiency virus (HIV) which causes acquired immuno-deficiency syndrom (AIDS).

BACKGROUND OF THE INVENTION

Acquired immunodeficiency syndrom (AIDS) is quite a new disease to humans and its epidemics are spreading on a worldwide scale in these years and causing tremendous impacts on the human society. A WHO report released March of 1987 reckoned that there are about one-hundred-thousand AIDS patients in the world and five- to ten-million carriers.

AIDS is a fatal disease caused by infection with human immunodeficienty virus (HIV), a retrovirus, a cardinal sign of which is serious immunosuppression complicated by opportunistic infections and malignant tumors such as Kaposi's sarcoma.

Involved in such opportunistic infections is a broad range of pathogenic microorganisms such as *Pneumocystis carinii*, protozoa, fungi, viruses, bacteria and so on, and as associated malignant tumors, Kaposi's sarcoma, non-Hodgikin's lymphoma, primary lymphoma, etc. are known.

The AIDS virus (HIV) is unusually liable to undergo mutation and its infection target cells are T-lymphocytes (helper T-cells) which play a leading role in mechanism of preventing infection. Since HIV belongs to a retrovirus, its gene is incorporated in the host cell gene. These multi-farious characteristics of HIV are intimately associated with the difficulties encountered in the treatment of this syndrome.

Researches directed to the treatment of AIDS are in progress on a worldwide scale. The antiviral agent, azidothymidine (AZT), for instance, has been clinically demonstrated to increase the life span of AIDS patients. However, its serious side effects such as bone marrow depression, anemia and neurologic disorders such as headache and convulsion have been posing problems in its clinical application. Aside from such therapy, various immunopotentiator therapies, vaccine therapies, and therapeutic modalities aimed at accompanying opportunistic infections and malignant tumors have also been attempted but none has proved to be a successful radial therapy of AIDS.

SUMMARY OF THE INVENTION

An object of the present invention is to provide an agent for treating viral infection, particularly, acquired immuno-deficiency syndrome (AIDS), which comprises as an active ingredient lactam compounds, more specifically, D-glucaro-δ-lactam, a salt or ester derivative thereof or 6-O-substituted-D-gluco-δ-lactam.

The present invention, thus, provides an antiviral agent comprising in an amount effective to therapeutically and/or prophylactically treat viral infection a lactam compound represented by formula (I)

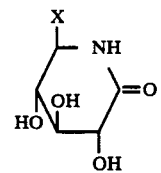

wherein X represents —COOR, wherein R represents a hydrogen atom or a straight-chain or branched-chain alkyl group having from 1 to 8 carbon atoms, or

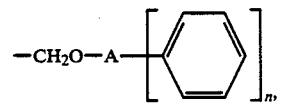

wherein n represents an integer of 2 or 3 and A represents methine when n is 2 or a quaternary carbon atom when n is 3.

DETAILED DESCRIPTION OF THE INVENTION

The compound according to the present invention is a glucarolactam or glucolactam derivative obtained by chemical modification of a naturally occurring substance and, hence, a departure from the hitherto-known compounds. The compound of the present invention has been found to significantly inhibit the destruction and death of human T-lymphocytes infected by the AIDS virus (HIV).

In formula (I), when X is —COOR, the compound is represented by formula (I')

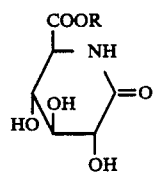

wherein R is as defined above. When X is

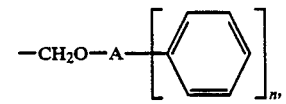

the compound is represented by formula (I'')

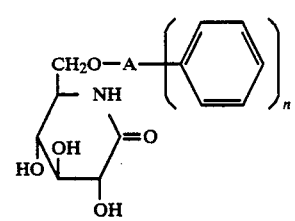

wherein n and A is as defined above.

The compound represented by formula (I') is a known compound and its efficacy as a β-glucuronidase inhibitor (JP-B-45-28375 and 56-34590 (the term "JP-B" used herein means an "examined published Japanese patent application"), J. Biochem., 72, 207–211, 1972) and its usefulness as an antiinflammatory agent (JP-A-

63-258421 (the term "JP-A" used herein means an "unexamined published Japanese patent application")) has been reported. The compound represented by formula (I″) is also the known compound and their efficacy as a leucocyte migration inhibitor as well as their usefulness as an anti-inflammatory agent has been reported (JP-B-56-17349 and JP-A-63-216867). It was found in the present invention that these compounds are effective for viral infections, particularly retroviral infections, and more specifically human immunodeficiency virus (HIV) infection.

D-glucaro-δ-lactam represented by the following formula (I′a) can be produced by chemo-enzymatic oxidation of nojirimycin (5-amino-5-deoxy-D-glucopyranose; formula (II)), which is a fermentative metabolite of *Streptomyces lavendulae* SF-425 which has been deposited at Fermentation Research Institute under the accetion No. FERM P-3096 (Tetrahedron, 23, 2125, 1968).

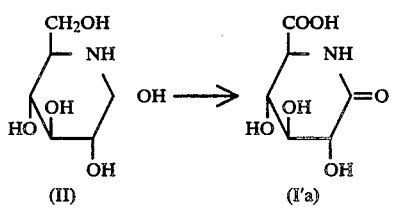

Nojirimycin represented by formula (II) is treated with glucose oxidase to give D-gluco-δ-lactam and, then, the thus-obtained compound was subjected to catalystic air oxidation to give D-glucaro-δ-lactam (Annual Report of Meiji Seika, 13, 80–84, 1973, JP-B-45-28375). D-gluco-δ-lactam can also be produced by reduction of 5-keto gluconic acid via the 5-oxime (JP-B-46-24382).

The D-glucaro-δ-lactam alkyl ester represented by formula (I′b) can be synthesized by reacting Dglucaro-δ-lactam (I′a) with an alkyl halide or a diazoalkane in a solvent such as methanol, tetrahydrofuran, dioxane, N,N-dimethylformamide or a mixture thereof (Nos. JP-B-56-34589 and 56-34590).

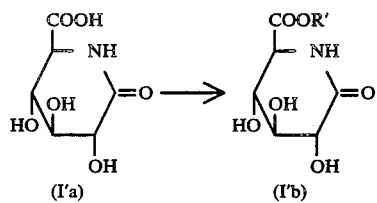

wherein R′ represents a straight or branched-chain alkyl group having from 1 to 8 carbon atoms.

As the pharmaceutically acceptable salt of D-glucaro-δ-lactam represented by formula (I′a), there may be mentioned an ammonium salt, alkali metal salts such as salts with sodium, potassium, alkaline earth metal salts such as salts with magnesium, calcium, salts with organic bases such as triethylamine, triethanolamine, diethylaminoethylamine, salts with heterocyclic amines such as piperidine, piperazine, morpholine, and salts with amino acids such as lysine and so on.

The compound represented by formula (I″) can be produced from D-gluco-δ-lactam.

Acquired immunodeficiency syndrom (AIDS) is a catastrophic disease which is immunological deficiency, mainly cellular immunodeficiency, caused by infecting immunocytes, particularly helper T-lymphocytes with human immunodeficiency virus (HIV) so that opportunistic infections and malignant tumors are liable to supervene and once the disease has had its onset, the patient has an almost 100% risk of death.

Azidothymidine (AZT) which is currently used in clinical practice has no effect on the host cells in which the HIV provirus has already been incorporated so that the administration of the agent to a patient with HIV infection must be continued throughout the remainder of his life. Therefore, the side effects of AZT on bone marrow pose the more serious problem.

The lactam compound of the invention has only a relatively low toxicity and is an agent with a very high safety margin. The compound may not only be administered alone but also be used in combination with other anti-AIDS agents such as AZT, 2,3-dideoxycytidine, 2,3-dideoxyadenine, interferons, interleukin-2 (IL-2) and so on.

For the treatment and prevention of viral infections the compound of the present invention can be administered orally or parenterally. The parenteral administration can be effected by intravenous, subcutanious, intradermal or intramascular injection, or in the form of suppositories. Particularly, the ester derivatives of the compound represented by formula (I′) are suited for oral administration.

Regarding the recommended dosage range for an adults, 100 to 3,000 mg is administered once a day or in a few divided doses. However, the optimum dosage should of course be determined according to the patient's age, body weight and clinical condition and the route and frequency of administration. Regarding the oral dosage form, capsules, tablets, granules, fine granules, poweders and so on can be used. These preparations may be formulated using excipients, lubricants, binders and the like. Examples of excipients include starch, lactose, mannitol, ethylcellulose, sodium carboxymethyl cellulose, and so on. Specific examples of lubricants include magnesium stearate and calcium stearate. Specific examples of binders include gelatin, gum arabic, cellulose ester, polyvinylpyrrolidone, etc. In the case of parenteral administration, sterile aqueous or non-aqueous solutions, suspensions or emulsions can be used. As vehicles for use in such non-aqueous preparations, there may be mentioned propylene glycol, polyethylene glycol, glycerol, olive oil, corn oil, ethyl oleate and so on. As vehicles for the suppositories, there may be mentioned cacao butter, Macrogol and so on.

The $LD_{50}$ value of D-glucaro-δ-lactam sodium salt in mice is not less than 3 g/kg by the intraveous injection and not less than 5 g/kg by the oral administration. The $LD_{50}$ value of D-glucaro-δ-lactam methyl ester in mice is not less than 5 g/kg by the intraveous injection and not less than 10 g/kg by the oral administration. With respect to 6-O-triphenylmethyl-D-gluco-δ-lactam, the $LD_{50}$ value is not less than 300 mg/kg in case of the subcutaneous administration in mice.

The antiviral agent according to the present invention comprises D-glucaro-δ-lactam, a salt or ester thereof or 6-O-substituted-D-gluco-δ-lactam as an active ingredient. The utility of this agent as a therapeutic and prophylactic agent for acquired immunodeficiency syndrom (AIDS) will be apparent from the in vitro anti-HIV activity data.

Namely, the host human T-lymphotropic MT-2 cell line is transplanted on a microtiter plate and a series of dilutions of the test compounds shown in the table below are added with or without addition of HIV, followed by incubation for 7 days. For evaluation, the residual viable cell count is then determined by colorimetry. The results are shown in the table below.

| Compound | $EC_{50}$ ($\mu g/ml$) | $IC_{50}$ ($\mu g/ml$) | $TI_{50}$ ($IC_{50}/EC_{50}$) |
|---|---|---|---|
| D-glucaro-δ-lactam calcium salt | $<2.5 \times 10^{-4}$ | $>2.5 \times 10^2$ | $>1.00 \times 10^6$ |
| 6-O-triphenylmethyl-D-gluco-δ-lactam | $3.86 \times 10^{-5}$ | $3.17 \times 10$ | $8.19 \times 10^5$ |

In the above table, $EC_{50}$ means the concentration of the test compound giving a 50% decrease in the cytocidal effect of HIV and $IC_{50}$ means the concentration of the test compound giving a 50% inhibition of growth of normal non-infected cells.

The following references and working examples are further illustrative of the present invention, but are no way intended to limit the scope of the present invention.

REFERENCE EXAMPLE 1

In 300 ml of water was dissolved 9 g of nojirimycin (5-amino-5-deoxy-D-glucopyranose) followed by addition of 30 g of barium benzoate and, under ice-cooling, further by dropwise addition of 3 ml of bromine. After the reaction at room temperature for 30 hours, the reaction mixture was neutralized with 5 N sulfuric acid and the resulting precipitate was filtered off. The filtrate was washed with chloroform and, then, stirred with addition of 22 g silver carbonate. The resulting precipitate was filtered off and the filtrate was passed through a column of Amberlite IR-120 (H-form, 100 ml). The effluent was combined with washings and concentrated, and the concentrate was crystallized from water-methanol to give 6.5 g of D-gluco-δ-lactam.

REFERENCE EXAMPLE 2

In 400 ml of distilled water was dissolved 9 g of D-gluco-δ-lactam, followed by addition of 3 g of hydrogenated platinum oxide. With the pH of the mixture being maintained at pH 8 to 9 with 2 N sodium hydroxide, the reaction was conducted by bubbling oxygen gas into the mixture with stirring at 60° to 65° C. for 3.5 hours. The catalyst was filtered off and the filtrate was decolorized with activated carbon and concentrated to dryness. The above procedure yielded 9.2 g of sodium salt of D-glucaro-δ-lactam.

REFERENCE EXAMPLE 3

To a solution of 1.8 g D-glucaro-δ-lactam in 20 ml of N,N-dimethylformamide were added 2.5 g of $K_2CO_3$ and 3 g of ethyl iodide and the reaction was conducted at 50° C. with stirring for 10 hours. The insolubles were filtered off and the filtrate was concentrated. The residue was extracted with 50 ml of warm ethanol and the extract was concentrated to about 10 ml and, then, caused to precipitate from ethyl ether. The procedure gave 1.4 g of D-glucaro-δ-lactam ethyl ester.

Thin-layer chromatography on silica gel (chloroform/methanol=4/1): Rf 0.17

| Potassium salt of D-glucaro-δ-lactam | 100 mg |
|---|---|
| Lactose | 100 mg |
| Potato starch | 75 mg |
| Polyvinylpyrrolidone | 10 mg |

-continued

| Magnesium stearate | 2.5 mg |
|---|---|

Potasium salt of D-glucaro-δ-lactam, lactose and potato starch were mixed and evenly wetted with a 20% solution of polyvinylpyrrolidone in ethanol. The mixture was passed through a 1 mm sieve, dried at 45° C. and passed through a 1 mm sieve again. The resulting granules were mixed with magnesium stearate and compression-molded to gave tablets.

EXAMPLE 2

In 150 mM sterile, pyrogen-free phosphate buffer (pH 7) was dissolved 100 mg of sodium salt of D-glucaro-δ-lactam, followed by addition of a solution of 5 mg sodium pyrosulfite. The mixture was passed through a sterile micropore filter (0.22 $\mu m$) into sterile glass vials and, after nitrogen purging, aseptically sealed to give a preparation for injection (total amount of 20 ml).

EXAMPLE 3

The following composition was filled into hard gelatin capsules to give an encapsulated preparation.

| D-Glucalo-δ-lactam ethyl ester | 200 mg |
|---|---|
| Lactose | 50 mg |
| CMC calcium | 100 mg |
| Magnesium stearate | 3 mg |

EXAMPLE 4

Tablets each containing the following composition were prepared.

| 6-O-triphenylmethyl-D-gluco-δ-lactam | 200 mg |
|---|---|
| Lactose | 75 mg |
| Potato starch | 50 mg |
| Polyvinylpyrrolidone | 15 mg |
| Magnesium stearate | 3 mg |

6-O-triphenylmethyl-D-gluco-δ-lactam was ground and mixed with lactose and potato starch. After a solution of polyvinylpyrrolidone was added thereto, the mixture was mixed and passed through a 1 mm sieve, dried in vacuum at 45° C. and passed through a 1 mm sieve again. The resulting granules were mixed with magnesium stearate and compression-molded to give tablets.

While the invention has been described in detail and with reference to specific embodiments thereof, it will be apparent to one skilled in the art that various changes and modifications can be made therein without departing from the spirit and scope thereof.

What is claimed is:

1. A method of treating viral infection which comprises administering to a host so infected an effective amount of D-glucaro-δ-lactam compound represented by formula (I')

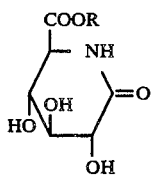 (I')

wherein R represents a hydrogen atom or a straight-chain or branched-chain alkyl group of 1 to 8 carbon atoms, or a pharmaceutically acceptable salt.

2. The method of treating viral infection according to claim 1, wherein said viral infection is human retrovirus infection.

3. The method of treating viral infection according to claim 1, wherein said viral infection is human immunodeficiency virus (HIV) infection.

4. A method of treating viral infection which comprises administering to a host so affected an effective amount of D-gluco-δ-lactam derivative represented by formula (I'')

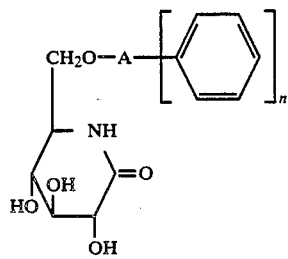 (I'')

wherein n represents an integer of 2 or 3 and A represents methine when n is 2 or a quaternary carbon atom when n is 3.

5. The method of preventing viral infection according to claim 4, wherein said viral infection is human retrovirus infection.

6. The method of preventing viral infection according to claim 4, wherein said viral infection is human immunodeficiency virus (HIV) infection.

* * * * *